United States Patent [19]

Geimer et al.

[11] Patent Number: 4,639,422

[45] Date of Patent: Jan. 27, 1987

[54] CELL CULTURE FILTER APPARATUS AND METHOD

[75] Inventors: Raymond C. Geimer, Mehlville; William R. Tolbert, Manchester, both of Mo.

[73] Assignee: Monsanto Company, St. Louis, Mo.

[21] Appl. No.: 825,717

[22] Filed: Feb. 3, 1986

[51] Int. Cl.[4] .............................................. C14M 3/02
[52] U.S. Cl. .................................................... 435/286
[58] Field of Search ............... 435/286, 241, 240, 284, 435/285, 311

[56] References Cited

U.S. PATENT DOCUMENTS

| 2,958,517 | 11/1960 | Harker et al. | 435/286 |
| 3,039,932 | 6/1962 | McLimans et al. | 435/286 |
| 4,166,768 | 9/1979 | Tolbert et al. | 435/286 |
| 4,178,209 | 12/1979 | Tolbert et al. | 435/241 |
| 4,184,916 | 1/1980 | Tolbert et al. | 435/241 |
| 4,289,854 | 9/1981 | Tolbert et al. | 435/241 |

OTHER PUBLICATIONS

Tolbert et al., Biotech. Bioeng. XXIV, 1671-1679 (1982) Tolbert and Feder, Ann. Rept. Ferm. Proc., vol. 6, Ch. 3, pp. 35-74 (1983).
Harakas, Ibid. vol. 7, Ch. 7, pp. 159-211 (1984).

Primary Examiner—James C. Yeung
Attorney, Agent, or Firm—Scott J. Meyer; James W. Williams, Jr.

[57] ABSTRACT

Cell culture filter apparatus and method is disclosed for the large scale cultivation of mammalian cells. This system is adapted for convenient manual assembly - disassembly of internal parts and interchangeability of filtration units.

6 Claims, 7 Drawing Figures

CELL CULTURE FILTER APPARATUS AND METHOD

BACKGROUND OF THE INVENTION

This invention relates to a novel cell culture system and more particularly to improved continuous cell culture filter apparatus and method which is useful in the large scale cultivation of mammalian cells.

The development of reactors and related apparatus for growing in culture large quantities of the fragile, complex cells that synthesize commercially valuable proteins is of significant importance in recent years. Methods for such large scale growth of mammalian cells are well-known and are described, for example, in several articles by Tolbert et al., *Biotech. Bioeng. XXIV*, 1671–1679 (1982); Tolbert and Feder, *Ann. Rept. Ferm. Proc.*, Vol. 6, Ch. 3, pp. 35–74 (1983); Harakas, *Ibid.*, Vol. 7, Ch. 7, pp. 159–211 (1984); and references cited in said publications.

The use of a cell culture reactor with controlled agitation by means of a magnetic stirrer bar or a mechanically driven impeller on a shaft is a typical feature of suspension cell culture apparatus. Examples of such apparatus are described in U.S. Pat. Nos. 2,958,517; 3,039,932; 3,572,651; 3,622,122; and 3,649,465. These are essentially batch type spin culture devices or spinner flasks in which the cells are incubated in a fixed amount of nutrient under appropriate culture conditions until cell growth has ceased.

Continuous cell culture systems and apparatus also have been described heretofore in which fresh medium can be added and spent medium can be separated from the growing cells by filtration and withdrawn from the flask on a continuous or semi-continuous basis as seen from U.S. Pat. Nos. 4,166,768 and 4,178,209.

In order to provide a gentle agitation of the suspension cell culture system, apparatus has been developed with flexible sheets on the agitator arm which are adapted to flex and billow like a sail with the liquid flow during rotation of the agitator arm as disclosed in U.S. Pat. No. 4,289,854.

Notwithstanding the advantages of the aforesaid cell culture system with the flexible agitator sheets, difficulties have arisen with the assembly - disassembly capability of the apparatus. It is desired to alleviate these difficulties and to improve the apparatus for commercial use in the production of medically important proteins and hormones. Complete cleaning of the apparatus between various cell culture runs to satisfy Food and Drug Administration (FDA) validation would be facilitated by improved assembly - disassembly capability of the apparatus.

BRIEF SUMMARY OF THE INVENTION

In accordance with the present invention an improved continuous cell culture filter apparatus and method is provided for the large scale cultivation of mammalian cells. This system is adapted for convenient manual assembly - disassembly of internal parts and interchangeability of filtration units.

The apparatus of this invention thus comprises:

(A) a hollow vessel having an opening at the top, (B) a stationary, hollow shaft means positioned within said vessel in fluid communication with said top opening of said vessel and supported downwardly therefrom without any lower bearing, (C) a stationary filter unit supported downwardly from said shaft means without any lower bearing and without any moving seals between the filter unit or any moving filter support means which could contact the cell suspension, said filter having (1) a fluid collection cavity in direct communication with the interior of said shaft means and the top of said vessel, and (2) a porous outer surface having a pore size smaller than the cells to be cultured or the carrier particles upon which said cells are attached but sufficiently large to permit permeation of fluid into said fluid collection cavity, (D) a rotatable agitator means supported downwardly from said shaft means and concentrically disposed about said filter unit for rotation by suspension from bearing means having low-friction engagement with said hollow shaft means, (E) said shaft means having a boss section positioned between said filter unit and said bearing means and a spring seat adaptable for holding spring means positioned between said boss section and said filter unit, (F) said agitator means having suspended thereon a plurality of flexible vanes which are substantially equidistantly spaced apart circumferentially and which extend substantially throughout the length of said filter unit, said vanes being held between a pair of disc-like holding means at each of the upper and lower ends of the vanes and transverse to the axis of said agitator means, with the lower member of the upper pair and the upper member of the lower pair of said holding means having side slits circumferentially spaced apart to receive the widths of said vanes, and said vanes having elastomeric means at each end compressed between the corresponding pair of said holding means.

The foregoing apparatus can be used for carrying out the filtration step in the method of culturing animal cells in agitated liquid suspension of nutrient culture medium in a batch or continuous system.

DETAILED DESCRIPTION OF THE INVENTION

While the specification concludes with claims particularly pointing out and distinctly claiming the subject matter regarded as forming the present invention, it is believed that the invention will be better understood from the following description taken in connection with the accompanying drawings in which:

Figure 1:
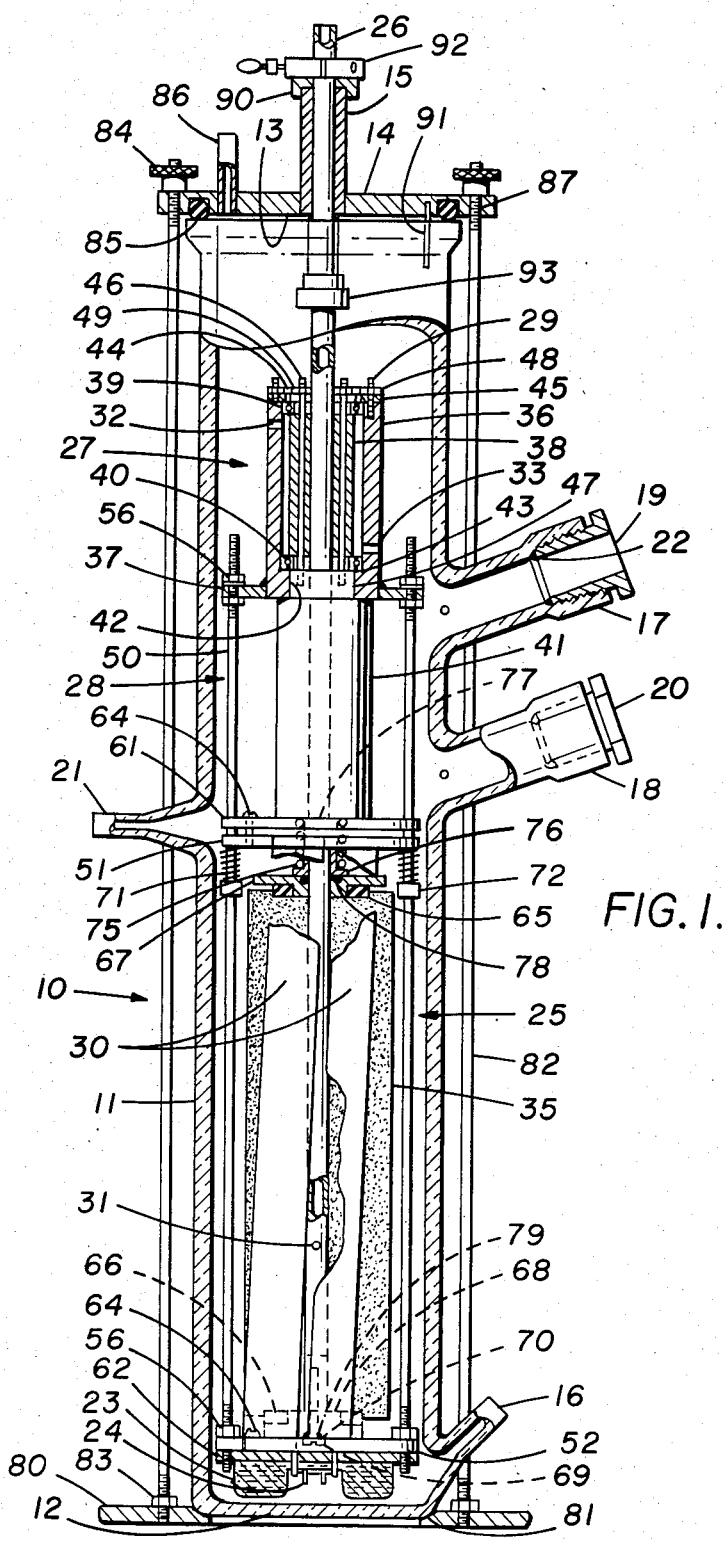
FIG. 1 is a side elevation view partly in cross section showing an embodiment of the cell culture filter apparatus of the present invention.

Now with particular reference to FIGS. 1 to 6, reference numeral 10 refers generally to a cell culture filter vessel which can be used in the continuous suspension culture of mammalian cells. It is especially adapted for use as a satellite vessel in a series with other cell culture reactors by suitable tubing means. For example, cell culture vessel 10 can serve as a filtering means for a main cell culture vessel (not shown) used for the growth of the cells. Vessel 10 preferably is made of clear glass or non-toxic rigid plastic materials but can also be made of biocompatible metals such as, for example, stainless steel. Vessel 10 is shown to have a generally cylindrical form with sidewalls 11, bottom 12 and mouth 13. The mouth is shown to be closed with a cover plate 14 having a raised tubular section 15 at its center.

The cell culture filter vessel 10 is also equipped with a plurality of openings in the sidewalls. Thus, a tubular port 16 near the bottom of the vessel can be used for the addition or removal of culture fluid through a line to the main culture reactor (not shown). Additional ports as may be desired for fluid transfer and the like can be disposed in the sidewalls. In the illustrative embodiment of FIG. 1, two upper side tubular ports 17 and 18 are adapted to receive fluid level probes at 19 and 20, respectively, which are used to determine the fluid level in the cell culture vessel. For convenience, these probes can be held in ports 17 and 18 by any convenient means such as, for example, rubber stoppers or by a compressible O-ring seal 22 in the port adapted for squeezing against a slidable insert which contains the probe. Another tubular port 21 for circulation of culture fluid is shown on the opposite sidewall in the embodiment of FIG. 1.

Positioned vertically in the cell culture filter vessel 10 is a rotatable agitator unit 25 which is peripherally suspended around an elongated, stationary shaft 26. The agitator unit comprises an agitator frame suspender 27, an open peripheral agitator frame 28, a magnet 23, and a plurality of flexible sails or vanes 30.

Elongated hollow shaft 26 is shown to have small holes 31 placed through both sides of the shaft in the lower portion of the vessel. These openings permit the withdrawal of filtered culture fluid from the vessel chamber at the top by passage through the bore of shaft 26.

Also positioned vertically within cell culture vessel 10 and suspended peripherally around shaft 26 within the agitator frame is a stationary replaceable filter unit or cartridge 35. The filter unit is shown to have a generally cylindrical body with an internal collection cavity. It is preferably made of microporous porcelain, sintered stainless steel, Teflon ® plastic or other such microporous filter materials. By locating the holes 31 so that they open into the cavity of filter unit 35, spent culture fluid can be filtered and withdrawn through shaft 26.

The agitator frame suspender 27 comprises a generally cylindrical, rotatable outer tube 36 with an enlarged diameter annular flange 37 at its base, a fixed concentric inner sleeve 38 and a pair of ball bearing assemblies 39 and 40 disposed between and at opposite ends of said inner sleeve and said outer tube. Tube 36 is concentric to shaft 26 and positioned so that it bottoms slightly above the enlarged diameter section 41 of said shaft. Sleeve 38 has reduced outer diameter portions at opposite ends for accomodating bearings 39 and 40. The bearings are further held in place by a reduced inner diameter section 42 of tube 36 at its bottom, an internal O-ring 43 seated on said tube bottom and annular concentric bearing clamp plates 44 and 45 at the top of tube 36. The outer diameter of clamp plate 44 is slightly less than the inner diameter of clamp plate 45 to permit bearing race independence and distribution of thrust between bearings 39 and 40. Inner clamp plate 44 has three holes equidistantly spaced apart circumferentially to receive three threaded rods 46 which are fastened into the upper rim or boss 47 of enlarged tube section 41. Nuts 49 with corresponding lock washers then secure plate 44. Additional hold-down rods with fasteners can be utilized if desired, but a plurality of three is preferred. Outer clamp plate 45 likewise has three holes equidistantly spaced apart circumferentially to fit over three threaded studs 29 in the upper rim of tube 36 which receive three nuts 48 with corresponding lock washers that fasten plate 45 to tube 36.

Suitable clearance for rotation of tube 36 around stationary sleeve 38 is maintained by the seating of the bottom of the inner race of lower bearing 40 on the upper boss 47 of tube section 41. O-ring 43 serves to pre-load the bearing assemblies so that the outer races rotate with tube 36. The inner races are held together by mechanical pressure as the inner clamp plate 44 presses down on upper bearing 39. This configuration of the bearing assembly avoids the use of a conventional press-fit and facilitates the rapid assembly - disassembly feature of the present invention. Tolerances on the parts are maintained to enable slip fit of bearings over parts by hand.

In order to facilitate autoclaving or steam sterilizing of the internal agitator frame suspender parts, tube 36 is provided with upper opening 32 and lower opening 33 through opposite side walls.

Figure 2:
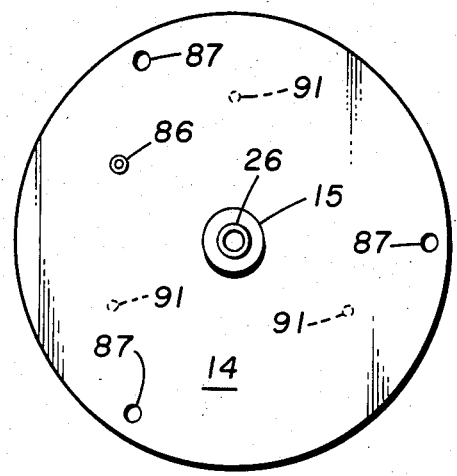
FIG. 2 is a top view of the apparatus of FIG. 1.

The agitator frame 28 comprises a plurality of three rods 50 which pass through holes 34 equidistantly spaced apart circumferentially in flange 37. The agitator frame is suspended downwardly from agitator suspender 27 and adapted to hold a plurality of flexible vanes 30. Preferably, about 3 to 12 vanes are employed. Illustratively, six vanes are shown to be vertically suspended between an upper annular vane clamp plate 51 and a lower annular vane clamp plate 52 fixed in the agitator frame. For clarity, only two vanes are shown in the view of FIG. 2. Upper annular vane clamp plate 51 has three holes 53 equidistantly spaced apart circumferentially to receive rods 50. Lower annular vane clamp plate 52 similarly has three threaded holes 58 for attachment to rods 50. As can best be seen in FIGS. 4 and 5, each said clamp plate also has six slits 54 tangentially cut through the plate thickness and extending into the side to a depth sufficient to accomodate the width of vane 30. Each said slit is shown to terminate in a small hole 55 which can be optionally formed in the plate for mechanical relief. The slits are thus preferably cut in from the outer side of the plate at an angle of from about 5 to about 45 degrees from a tangent to the outer entry of the slit. Adjustments in this angle provide for holding fewer or more than the six vanes illustrated with the angle shown in FIGS. 4 and 5. Clamp plates 51 and 52 are positioned in the agitator frame so that the leading edge of the vane at the bottom is forward of the leading edge of the vane at the top, whereby the angle of the vanes during clockwise rotation of the agitator unit will cause liquid to move upward and radially into the filter unit. Rods 50 are threaded at both ends to be fastened to the annular flange 37 and plate 52 with nuts 56.

The flexible vanes 30 can be made of fine mesh cloth or fabric, plastic film or metal foil, and other such permeable or impermeable flexible sheet materials, for example, a nylon screen cloth or a flexible fiberglass sheet. A monofilament screen nylon cloth available under the trademark NITEX® from Tetko, Inc., of Elmsford, N.Y., having nominal mesh openings of about 110μ and a thickness of about 0.005 inch (0.0127 cm) is eminently suitable for this purpose.

Figure 3:
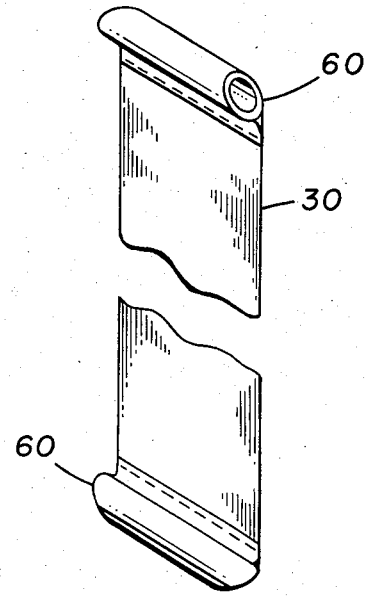
FIG. 3 is a perspective view partially cutaway showing an agitator vane of FIG. 1.
Figure 4:
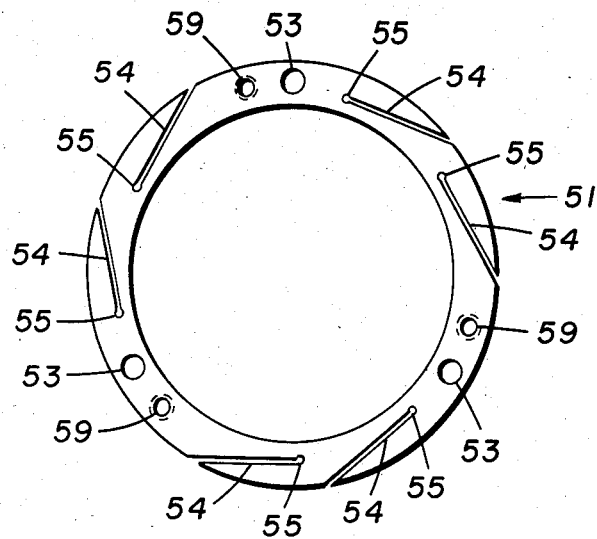
FIG. 4 is an end view of an upper clamp plate for a plurality of agitator vanes of FIG. 3.
Figure 5:
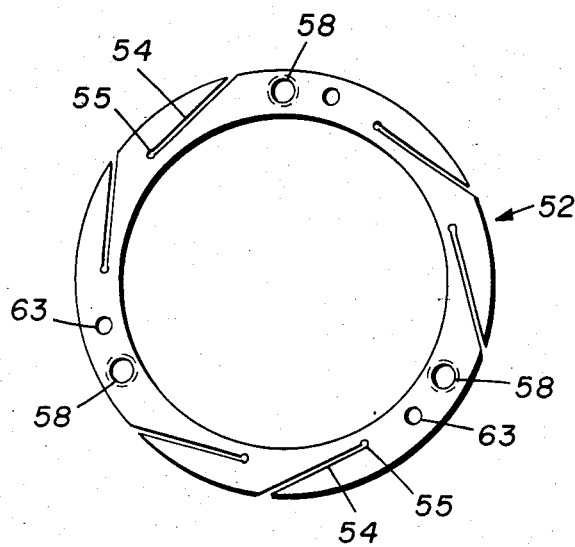
FIG. 5 is an end view of a lower clamp plate for a plurality of agitator vanes of FIG. 3.
Figure 6:
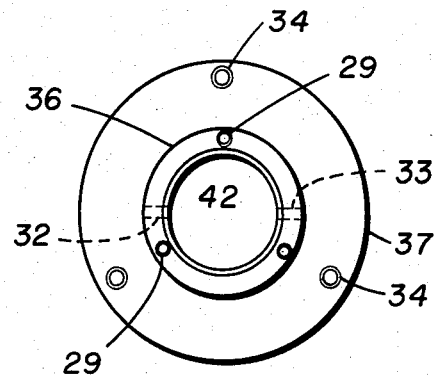
FIG. 6 is an end view of the agitator frame suspender of FIG. 1.

As can best be seen in FIG. 3, an elastic tube 60, which can be solid or hollow, is sewn into each of the ends of vanes 30. The vanes are then held into position in the agitator frame as these tubes are squeezed between a set of upper clamp plates 51 and 61 at one end and between a set of lower clamp plates 52 and 62 at the other end. Clamp plates 52 and 61 have three holes 63 equidistantly spaced apart to receive screws 64 which hold together upper plates 51 and 61 and lower plates 52 and 62 as they screw into tapped holes in plates 51 and 62.

In a preferred embodiment of the invention, upward tension on the flexible vanes 30 is provided by placement of tension springs 71 on rods 50 directly beneath the vane clamp plate 51. Collars 72 on rods 50 are adapted to support these tension springs. Such spring loading of the upper clamp plates facilitates maintenance of the vanes in the preferred configuration during all operating conditions.

A ceramic type magnet 23 which is coated with a material that is non-toxic to the cells such as Teflon, is shown to be affixed to the bottom of clamp plate 62 by suitable holding means 24. The holding means can comprise a spring clip positioned between several vertical pins held in clamp plate 62 as shown in FIG. 1 or other such conventional holding means. The agitator unit 25 can be caused to rotate about shaft 26 by activation of a revolving U-shaped, ring shaped or bar magnet (not shown), positioned under the cell culture filter vessel 10. Alternatively, a plurality of magnet stir bars (not shown) can be fastened to the bottom of clamp plate 62 or otherwise held at the bottom of the agitator unit 25.

Provision is made in the cell culture filter vessel 10 to allow for physical changes in the size of a plastic disposable filter cartridge and for interchangeability between plastic disposable filters and solid porcelain filters. In the embodiment shown in FIG. 1, the cell culture vessel is adapted for suspension of a disposable plastic filter 35 inside the agitator frame 28. The filter cartridge with rubber gaskets 65 and 66 placed around the upper and lower openings, respectively, of the filter, is clamped between annular upper filter seal plate 67 and annular lower filter seal plate 68. As the lower filter seal plate is fixed to the lower end of shaft 26 by a pan head screw 29, the top filter seal plate is adjustably held in position by a compression spring 75 carried between spring seat 76 and the bottom of the enlarged tube section 41. Lower boss 77 on tube section 41 serves to center spring 75. Spring 75 thus permits convenient changes in size of the filter cartridge. It also allows for expansion and contraction of the filter due to temperature changes during autoclaving procedures. Fluid tight engagement of the filter is provided by O-ring seal 78 positioned between spring seat 76 and an annular recess in the top of upper filter seal plate 67, by O-ring seal 79 positioned between an annular recess in the bottom of lower filter seal plate 68 and a washer 70 and pan head screw 69 placed through the center hole of filter seal plate 68 and tightened into the threaded opening of shaft 26.

For stability purposes, the cell culture filter vessel 10 is shown to rest on annular base 80 which has an internal beveled edge 81 to accomodate the curvature of the vessel bottom 12. Cover plate 14 is held over the vessel mouth 13 by a plurality of three rods 82 placed through holes 87 equidistantly spaced apart circumferentially in the cover plate and into corresponding holes in base 80. Rods 82 are threaded at the lower ends for fastening to the annular base with nuts 83. The cover plate is tightened over the culture vessel mouth by knurled knobs 84 which are threaded for engagement over the upper threaded ends of rods 82. A silicone rubber or other such compressible O-ring seal 85 positioned between a circumferential recess in the bottom of cover plate 14 and the rim of culture vessel 10 provides a fluid tight sealing engagement.

Cover plate 14 is provided with an opening to receive a vacuum/pressure line 86 which can be used to increase or reduce the liquid level in the culture vessel. A plurality of three short locating pins 91 equidistantly spaced apart circumferentially and extending downwardly from the underside of cover plate 14 are adapted to slidingly engage the inner walls of cell culture vessel 10 to facilitate proper positioning of the cover plate on the vessel.

Ease of assembly - disassembly of the cell culture apparatus of the present invention is further provided for by external shim 90, clamp 92 and an internal O-ring tube fitting assembly 93 for shaft 26 on the lower side of cover plate 14 to establish magnet clearance at the bottom of vessel 10.

Figure 7:
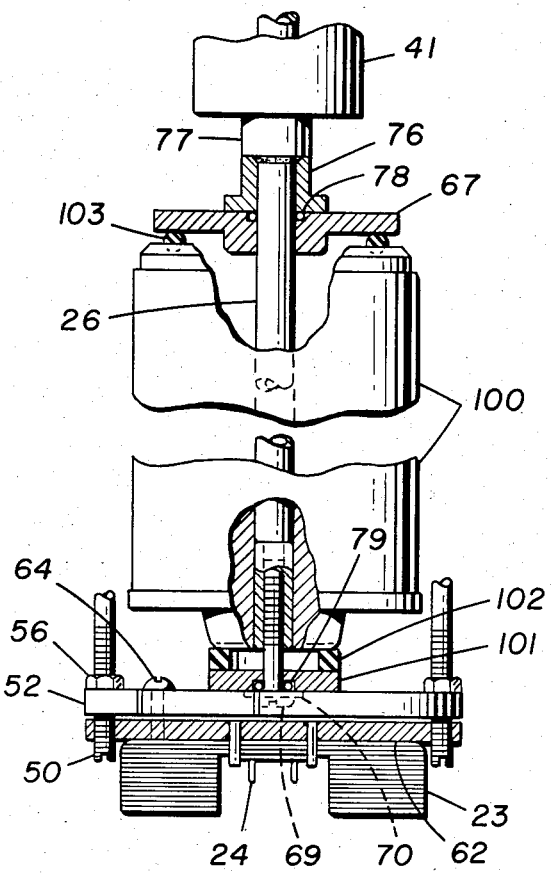
FIG. 7 is a side elevation view partly in cross section and partially cutaway showing another embodiment of a filter unit adapted for the apparatus of FIG. 1.

In another embodiment of the invention as shown in FIG. 7, in which parts similar to those in FIG. 1 are shown with similar reference numerals, a microporous porcelain filter cartridge 100 can be suspended peripherally around central shaft 26 and clamped between annular upper filter seal plate 67 and a modified lower filter seal plate 101. In this embodiment the filter cartridge rests on a rubber gasket 102 positioned between the lower edge of the filter and plate 101. At the top of the filter a rubber O-ring seal 103 is positioned between plate 67 and an annular recess in the upper rim of the filter cartridge. The compression spring is dispensed with in the embodiment of FIG. 7 and the spring seat 76 is held directly against the bottom of the lower boss 77 of the enlarged diameter section 41 of shaft 26.

In operation, the cell culture apparatus of the present invention provides an improved method for controlling liquid culture media movement by establishing equilibrium between the cell culture filter vessel 10 and a main cell culture reactor (not shown). The system can operate as a cell culture perfusion chemostat system without the use of pumps, valves, or other devices under the liquid level which grind cells by reversing pressure differential above the liquid level in filter vessel 10 employing sterile air and/or vacuum at line 86 and level probes at 19 and 20. Thus, a vacuum can be pulled on the system to draw liquid to the level of the upper probe at 19 and, alternately, pressure can be applied until the liquid level falls to the level of the lower probe at 20.

During operation of the cell culture apparatus in another mode, continuous flow of medium to establish equilibrium can be conveniently maintained by drawing in culture medium at port 16 and expelling culture medium at port 21 by the use of external one-way flow valves (not shown).

It will be appreciated that the cell culture method and apparatus of this invention is adaptable to use of any of the well-known tissue culture media such as, for example, Basal Medium Eagle's (BME), Eagle's Minimum Essential Medium (MEM), Dulbecco's Modified Eagle Medium (DMEM), Medium 199, RPMI medium 1640, and balanced salt solutions (BSS) such as those of Eagle and Hanks fortified with various nutrients. These are commercially available tissue culture media and are described in detail by H. J. Morton, *In Vitro* 6, 89-108 (1970). These conventional culture media contain amino acids, mineral salts, vitamins and carbohydrates and are frequently fortified with mammalian sera such as fetal bovine serum.

The present invention is adaptable to all types of animal cells, for example, mammalian, fowl and amphibian cells, as well as plant cells, e.g., carrot cells. Primary cells taken from embryonic, adult or tumor tissues as well as cells of continuous cell lines can thus be used. Examples of typical such cells are primary rhesus monkey kidney cells, baby hampster kidney cells, mouse embryo fibroblasts, normal human lung embryo fibroblasts, Hela cells, primary and secondary chick fibroblasts, and various cells transformed with SV-40 or polyoma virus, as well as recombinant cells prepared by genetic engineering. When using primary and non-continuous cell lines, it is generally preferable to include microcarriers in the culture media for cell attachment. As the cultured cells release valuable proteins and hormones into the culture medium, the spent culture medium can be withdrawn through the filter unit and separated from the cells and carried out into a satellite vessel, wherefrom the desired proteins and hormones are recovered by various conventional protein isolation and purification techniques.

Although various materials of construction of the apparatus of the invention are illustrated, it will be appreciated that various other materials can be used. The internal parts, however, should be constructed of materials compatible with the cells and culture medium.

Various other examples will be apparent to the person skilled in the art after reading the present disclosure without departing from the spirit and scope of the invention. All such other examples are included within the scope of the present invention.

What is claimed is:

1. Continuous cell culture filter apparatus adapted for convenient manual assembly - disassembly comprising:
   (A) a hollow vessel having an opening at the top,
   (B) a stationary, hollow shaft means positioned within said vessel in fluid communication with said top opening of said vessel and supported downwardly therefrom without any lower bearing,
   (C) a stationary filter unit supported downwardly from said shaft means without any lower bearing and without any moving seals between the filter unit or any moving filter support means which could contact the cell suspension, said filter having
      (1) a fluid collection cavity in direct communication with the interior of said shaft means and the top of said vessel, and
      (2) a porous outer surface having a pore size smaller than the cells to be cultured or the carrier particles upon which said cells are attached but sufficiently large to permit permeation of fluid into said fluid collection cavity,
   (D) a rotatable agitator means supported downwardly from said shaft means and concentrically disposed about said filter unit for rotation by suspension from bearing means having low-friction engagement with said hollow shaft means,
   (E) said shaft means having a boss section positioned between said filter unit and said bearing means and a spring seat adaptable for holding spring means positioned between said boss section and said filter unit,
   (F) said agitator means having suspended thereon a plurality of flexible vanes which are substantially equidistantly spaced apart circumferentially and which extend substantially throughout the length of said filter unit, said vanes being held between a pair of disc-like holding means at each of the upper and lower ends of the vanes and transverse to the axis of said agitator means, with the lower member of the upper pair and the upper member of the lower pair of said holding means having side slits circumferentially spaced apart to receive the widths of said vanes, and said vanes having elastomeric means at each end compressed between the corresponding pair of said holding means.

2. The cell culture filter apparatus of claim 1 including spring loaded means positioned beneath said upper disc-like holding means to maintain upward tension on said vanes.

3. The cell culture filter apparatus of claim 1 in which the agitator bearing means comprises an inner sleeve having frictional engagement with the hollow shaft means, an outer tube concentric to and having low friction engagement with said inner sleeve provided by disposition of a pair of ball bearing assemblies between and at opposite ends of said inner sleeve and said outer tube.

4. The cell culture filter apparatus of claim 1 in which the agitator vanes are supported by the holding means at the lower ends of said vanes ahead of the upper ends of said vanes relative to the direction of rotation of the agitator unit to provide culture fluid movement upward and radially into the filter unit.

5. The cell culture filter apparatus of claim 1 in which the bearing means comprises an inner sleeve having frictional engagement with the hollow shaft means, an outer tube concentric to and having low friction engagement with said inner sleeve provided by disposition of a pair of ball bearing assemblies between and at opposite ends of said inner sleeve and said outer tube and in which the agitator vanes are supported by the holding means at the lower ends of said vanes ahead of the upper ends of said vanes relative to the direction of rotation of the agitator unit to provide culture fluid movement upward and radially into the filter unit.

6. The cell culture filter apparatus of claim 5 including spring loaded means positioned beneath said upper disc-like holding means to maintain upward tension on said vanes.

* * * * *